United States Patent [19]
Watkins et al.

[11] Patent Number: 5,997,494
[45] Date of Patent: Dec. 7, 1999

[54] ORTHOPEDIC APPLIANCE TO ASSIST REDUCTION OF ANTERIOR DISLOCATION OF SHOULDER

[76] Inventors: Connie S. Watkins, 950 Faulkner; Randall G. Stearns, 1445 Woodland, both of Wichita, Kans. 67203

[21] Appl. No.: 09/002,642

[22] Filed: Jan. 5, 1998

[51] Int. Cl.$^6$ .......................... A61F 15/00; A63B 21/065
[52] U.S. Cl. ................................ 602/36; 482/105; 602/32
[58] Field of Search .................................. 602/20, 21, 32, 602/36; 482/50, 44, 105, 139

[56] References Cited

U.S. PATENT DOCUMENTS

| | | | |
|---|---|---|---|
| 4,756,527 | 7/1988 | Ledbetter | 482/139 |
| 4,941,464 | 7/1990 | Scott | 602/36 X |
| 5,090,691 | 2/1992 | Pollock | 482/139 |
| 5,096,190 | 3/1992 | Montgomery | 482/105 |
| 5,290,219 | 3/1994 | Hetrick | 602/32 |
| 5,419,756 | 5/1995 | MConnell | 602/36 |
| 5,501,656 | 3/1996 | Homma et al. | 602/36 X |

OTHER PUBLICATIONS

Flaghouse Rehab Spring 1995 Catalog, p. 18.

*Primary Examiner*—Richard J. Apley
*Assistant Examiner*—Denise Pothier
*Attorney, Agent, or Firm*—Bradley P. Sylvester

[57] ABSTRACT

An orthopedic appliance that is designed to assist in the reduction of an anterior dislocation, during a course of treatment given to a person who is laying horizontal on a table or similar elevated surface, with the affected arm hanging directly downward. The appliance eliminates the need for a person to grip or in any way consciously hold on to weighted objects, thereby allowing the patient to fully relax during the treatment procedure. The appliance comprises one or more forearm straps which are wrapped around the forearm of the person receiving treatment, where one or more weighted units are attached to the forearm straps, with extending supports so that the weights hang down, so that a direct downward pull on the affected arm is possible. Said weighted units may be attached to the forearm straps using one or more descending loops, in which weights such as dumbbells may be placed. In place of loops, weighted units may be hooked on to the forearm strap portion, with the weighted units supported so that they are positioned below the affected person's wrist and hand.

1 Claim, 3 Drawing Sheets

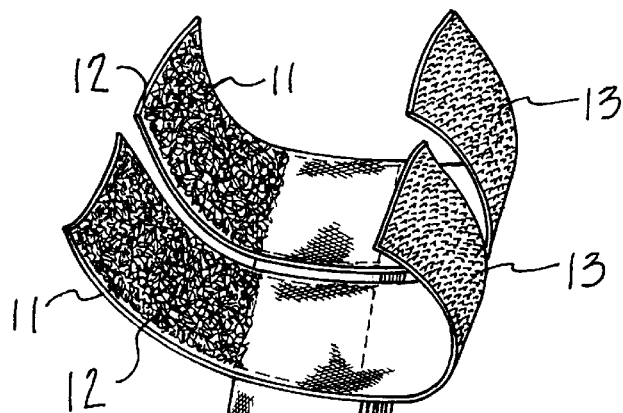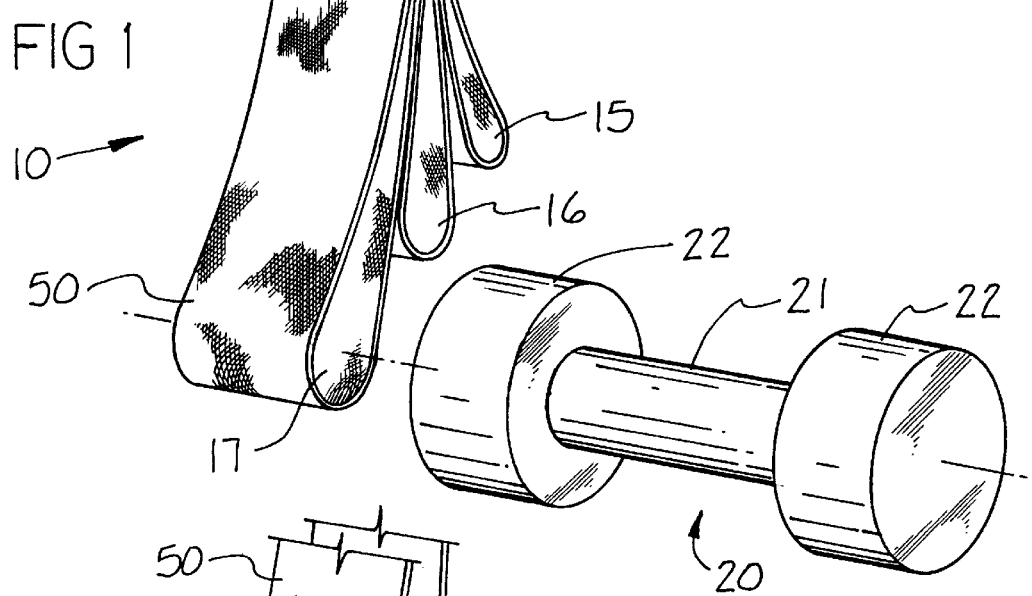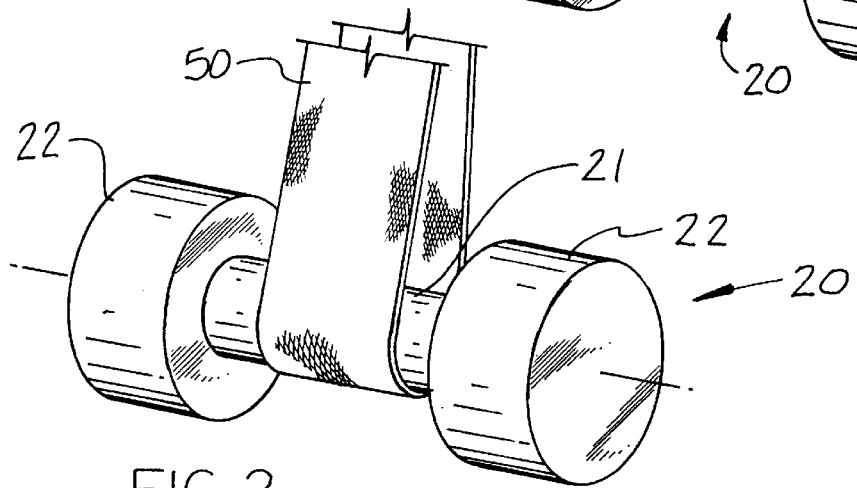

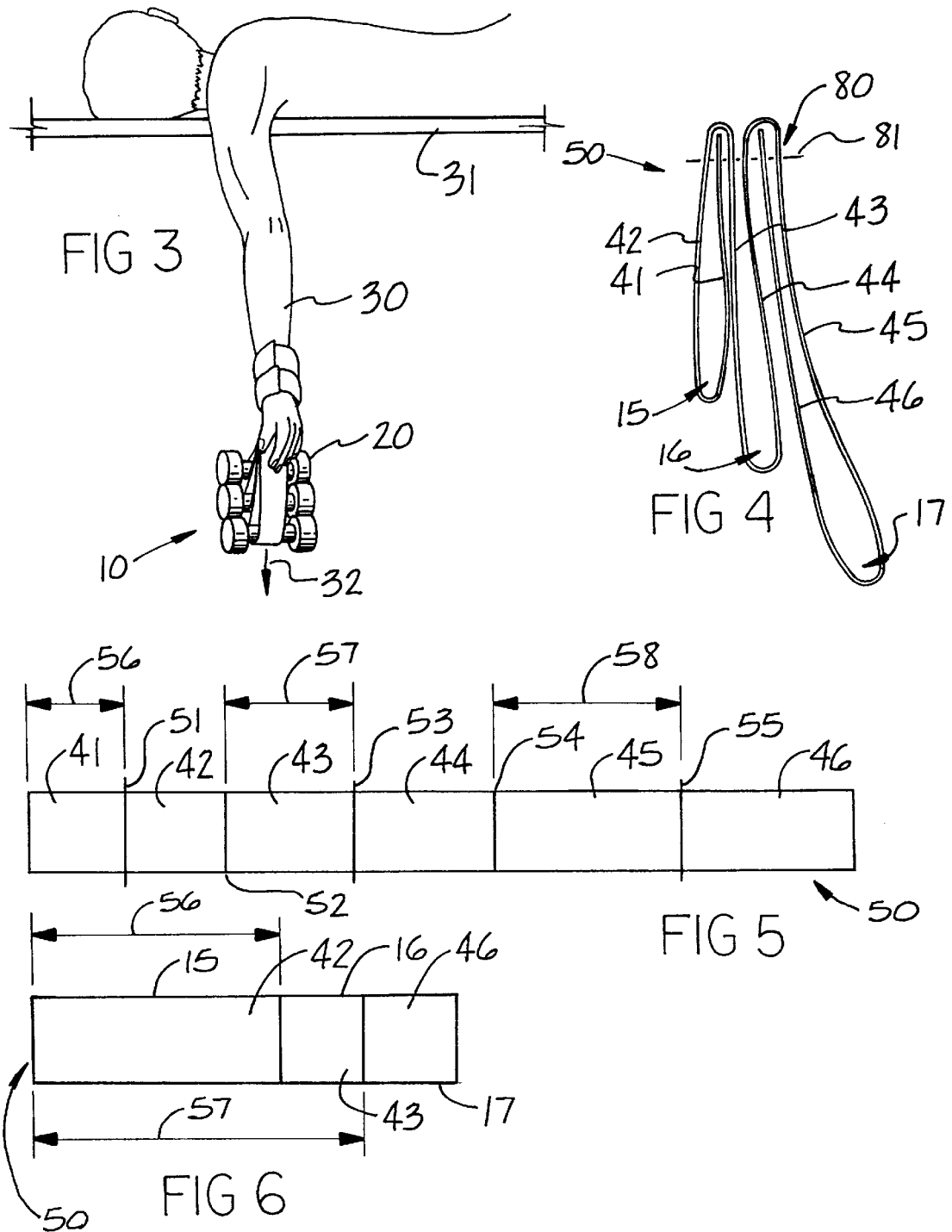

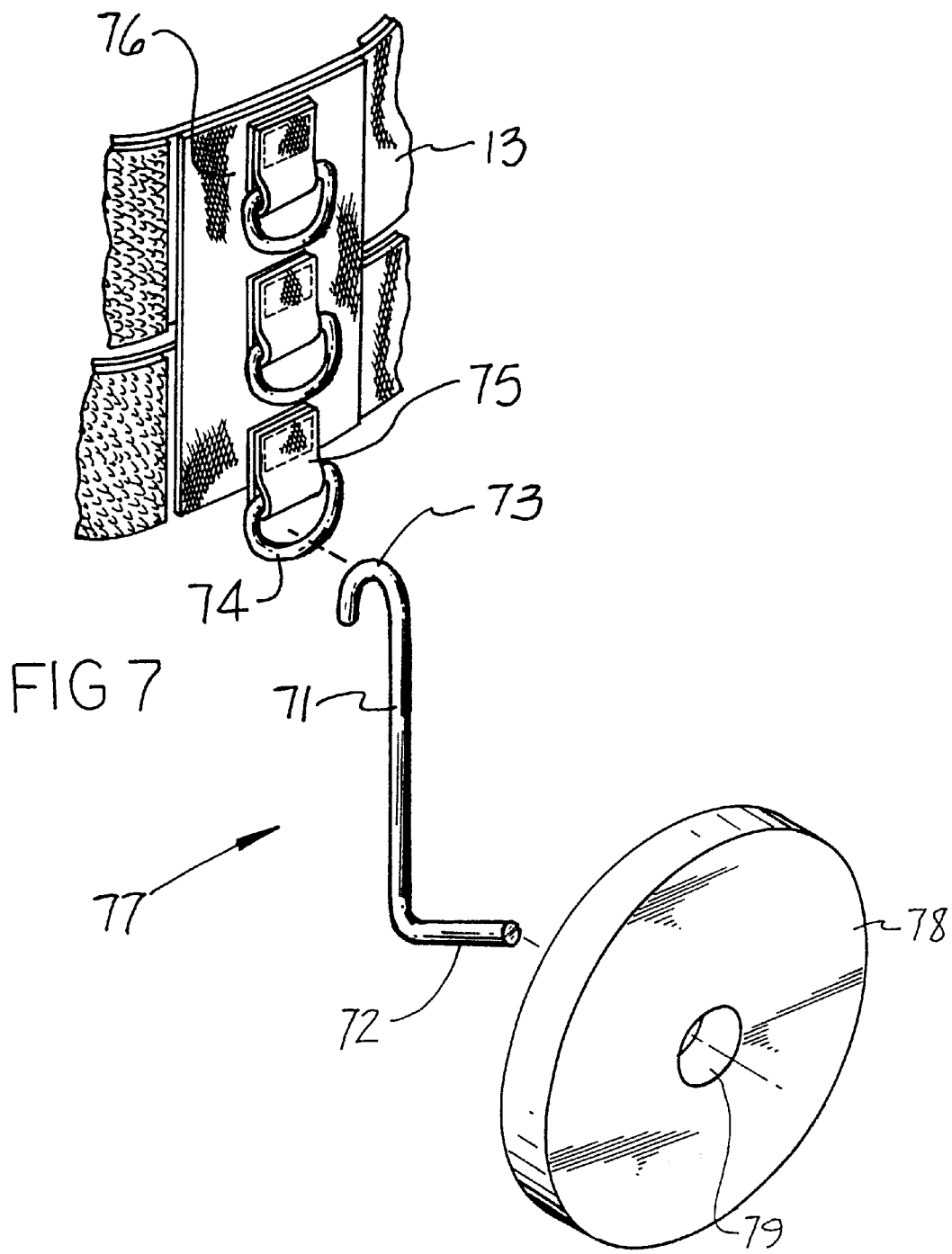

ORTHOPEDIC APPLIANCE TO ASSIST REDUCTION OF ANTERIOR DISLOCATION OF SHOULDER

BACKGROUND OF THE INVENTION

This invention relates to an orthopedic appliance that is designed to assist in the reduction of an anterior dislocation (sub coracoid dislocation) of a person's shoulder using what is known as the "Stimson Technique". Currently, hospitals and centers that provide medical assistance or treatment to persons involving dislocations of shoulders have turned to fixing weights of one type or another to a person's arm in order to achieve a downward pulling on the person's arm while they lay prone on a table or other surface. The maximum benefit of any weight utilized in this manner is realized by having the patient placed in a prone position on the edge of a table or gurney with the arm extending directly downwards. While the patient has weight pulling downward on their arm or hand, they are instructed to relax. The patients are expected to maintain this position for approximately ten to fifteen minutes, with muscle relaxation being a priority.

Hospitals and treatment facilities offering their services to injured persons have utilized weights anywhere from ten pounds up to twenty-five pounds, held by a person's hand to give the downward pull necessary to reduce the anterior dislocation. The weights that have been generally used have comprised such archaic methods as pails of water and dumbbells themselves that the person/patient is expected to hold. A bucket is used because the amount of weight can be varied proportionately to the volume of water placed into the bucket. The major drawback of such attempts has always been that the patient with the anterior dislocation is themselves forced to hold onto the weight, which can be a painful process to the patient, causing muscle relaxation to be more difficult to achieve.

Other methods such as providing traction to a person so that their arm is pulled upwards is shown and described in U.S. Pat. No. 4,616,637 (Caspari, et al.). This patent, which was issued in 1986, employs a forearm gripping device. The relevance of this prior art shows that a forearm can be wrapped with material to provide a means to grip the forearm while applying a pulling force. This particular device, however, had no means to direct the arm downwards and was more useful in simply holding an arm in an upward position during surgical procedures.

Various exercising devices exist, but which have not been readily utilized by medical treatment facilities. The common drawback for these existing exercising devices is the complexity of them and their inability to readily attach to an appendage concurrent with the inability to quickly and easily modify the amount of weight placed in the device or apparatus itself. U.S. Pat. No. 3,910,577 (Boyle) typifies a device which can be simply draped over a person's appendage containing pouches in which weights themselves may be placed therein. This would provide a resistance to upward movement to a person desiring to lift their leg or arm in an exercise maneuver. This particular device has little real use with the problem at hand in dealing with anterior dislocations, since there is no method for the Boyle device to be properly affixed to a person's arm for a direct downward pull on said arm.

Another device which was intended for use with a person's arm and hands in shown in U.S. Pat. No. 4,109,908 (Pugh, et al.). In Pugh, the user is required to grip a handle which stabilizes a weight holder platform that is strapped to a person's forearm on one end. While the device's benefits for exercising a person's forearms are evident, this particular device would still require a user to grip the handgrip and to maintain a continuing grip on said handgrip during the entire process in which a dislocation is being reduced. Since the purpose of a proper device is both to provide a downward pull while achieving relaxation of the patient, relaxation is once again unable to be fully achieved due to the person's need to utilize the forearm muscles to employ their fingers to grip the device.

A weighted cuff is depicted in U.S. Pat. No. 4,384,714 (Kimura). In Kimura, there is a thick plate-like main body that is formed that has a plurality of elongated holes which can receive weighted rods. The number of rods inserted in the receiving holes dictates the extent of weight being implied by the device to a person's appendage. This device has the drawback for being unable to provide sufficient amounts of weight to adequately reduce a person's anterior dislocation properly. The device shown in Kamura tends to be one that would simply make a person's movements during exercise more difficult, thereby increasing the stress on muscles being exercised and giving the user of this the benefit of an increased physical workout in a shorter period of time. A subsequent weighted exercise apparatus is shown in U.S. Pat. No. 4,858,916 (Beaumont). The Beaumont apparatus is similar to that shown in Pugh, et al., in that the user has a strap around their forearm with a means to grip and hold on to the apparatus itself utilizing a gripping bar. Weights may be incrementally added or reduced depending on the user's desire. This invention has the same limitations as does Pugh with regard to reducing anterior dislocations. This device has no means for the user to relax their forearm muscles, thereby allowing their fingers to relax as well. This device has the same drawbacks and problems as does using a bucket of water.

A weighted exercise glove is depicted and described in U.S. Pat. No. 4,368,883 (Tiktin). In Tiktin, the glove has attachment points by which the user may affix weights on various fingers. The glove itself is designed primarily to exercise individual fingers and muscles and corresponding muscles in a person's forearm. This device would have some difficulty in having sufficient weight attached to reduce an anterior dislocation, since a great deal of stress would be required to be placed on individual fingers, rather than on the more durable forearm bone structure.

A somewhat similar device to the Tiktin patent is shown in U.S. Pat. No. number 5,004,227 (Hoffman). In Hoffman, an exercise apparatus comprises a glove like apparatus in which the back of the hand and palm area provides support for attachment of weights which are affixed within a pocket in the glove. This device has the drawback of being unable to position the weights directly downward of the arm itself so that if sufficient weights were utilized in the pouch area of the Hoffman apparatus, the pull on the arm would be off center from the arm, and fail to provide a direct downward pull. In addition, the pull should be limited to the arm, rather than the wrist alone. To maximize reduction of an anterior dislocation, the weight must be positioned so that it is providing a direct, downward pulling force uniformly around the circumference of the arm itself, rather than weights being distributed on one external side and providing a pulling force on only one side.

SUMMARY OF THE INVENTION

This invention is directed toward assisting the reduction of an anterior dislocation of a person's shoulder using what is known as the "Stimson Technique". This technique involves the application of weight to a person's arm, to pull the arm directly downward, perpendicular to the body trunk which lays on a table or Gurney.

The appliance itself is comprised of one or more loops that are able to hold dumbbell weights or other similar weighted items, with one end of the loops attached to a means for gripping a person's forearm about the wrist and forearm area. The loops may be themselves stitched onto a single piece of resilient material or frame. A series of loops, however, may be created from a single strap of resilient material, with said resilient material folded at various points back on itself to create unshaped loops of various lengths, with all loops having folds that define the loops evenly positioned one with the other, so that their ends as defined by the folds, are situated evenly with respect to the other loops, where there is a plurality of loops. These evenly positioned ends and folds are stitched or affixed together, so that each loop in this appliance has both of its defining ends closed to create a continuous loop of resilient material.

The means for attaching this appliance to a person's forearm or wrist, preferably being one or more forearm straps, are attached to the loop closed ends, using stitching that binds the straps to the closed loop ends, or any other means or manner of affixing the forearm straps to the loop closed ends.

The loops are preferably of varied lengths so that any weighted material they receive and support does not interfere with or crowd out the weighted material residing in other loops. Dumbbells of known weight are typically the weighted material of choice to be used with this appliance, since dumbbells are common items, which have uniform weights given to them. For example, five pounds, ten pounds and fifteen pound dumbbells are of the size and weight that can be easily used with this appliance.

The use of this appliance is accomplished by having a patient lay horizontally on a table or Gurney, with the arm of the affected shoulder hanging directly downwards. This appliance is attached securely to the user's forearm area using an attachment means such as a set of straps that wrap around the forearm area, having a means to attach the strap ends to each other, where the means to attach the strap end to each other utilizes such attachment means as snaps or velcro brand type attachments.

Once the appliance is fixed to a person's forearm, a starting weight of ten pounds is added to this appliance, preferably using dumbbells of five or ten pound increments to give a total weight of ten pounds. Additional weight of five or ten pounds may be added as necessary depending on the extent of anterior dislocation, size of the patient and duration of time for the weight to be applied to the patient's arm, with subsequent dumbbells placed in their own loop. The dumbbells are slid through the loops so that the central handgrip is supported by the loop's strap width, with the bulbous ends of the dumbbell protruding outward from each side of the strap, with the bulbous ends being prevented from entering the area defined by the loop, thereby keeping the dumbbell from sliding out of the loop.

The width of the straps being used to hold the dumbbells should not exceed the width of the handgrip portion of the dumbbell. In this manner, the dumbbell bulbous ends will extend outward beyond the width of the strap loop on both sides of said strap loop, providing a stable support for the dumbbells, while preventing the dumbbells from readily sliding out of the strap loops.

While the appliance is fixed to the person's forearm, with proper weights/dumbbells inserted into the loops defined by the strap, the patient is intended to be able to remain as relaxed as possible during the entire procedure. Since the forearm straps secure the appliance to the forearm, the patient need not grip anything, and the ability to relax is maximized. Internal and external rotation of the shoulder during the procedure may aid in the reduction, along with the fact that a constant and uniform pull is being applied, pulling the arm directly downwards.

Following the completion of the procedure, the appliance may be removed with or without the weights remaining therein, and the patient is able to return to an upright sitting position for any further treatment he or she might need to receive.

The loops of this appliance may be formed from a continuous single strap that is folded at various intervals along its length back on itself so that a series of loops are created, where each loop has a length different from other loops adjacent to it. Using a single piece strap will provide the means to increase stability of this invention, as well as decrease the stress points of this invention that would be subject to wear and tear, causing the loops to detach from each other. A single piece of strap further allows easier manufacture of this appliance with its weight carrying and supporting capacity maximized.

A variation of the weight holding portion of the invention may also be comprised of one or more loops that are fixed to the portion of the strap that encircles the user's forearm, with weight able to be hooked on to the strap. Typically, a weighted material is placed onto an extender, which has a means to hold the weighted material on one end, and a means to attach to the strap on the other end, such as a curved end portion that is able to hook through the loop on the strap. Weights are able to be removed by simply unhooking them from the strap. Any other type of obvious attaching method would also be satisfactory, such as snaps or Velcro type surfaces.

This appliance is intended to provide the means to utilize common ordinary weights that are available for purchase and to be incorporated with the use of this appliance. It is an object of this invention to provide a stable weighted appliance to reduce anterior dislocation, by providing a direct downward pull on a person's wrist.

It is the further object of this invention to provide an appliance to assist in the reduction of anterior dislocation, whereby the device provides as little stress as possible to the user/patient, allowing them to relax entirely during the procedure.

It is a further object of this invention to provide an appliance to reduce anterior dislocation of a person's shoulder in which weights of various but uniform increments may be applied to the apparatus so as to provide a set uniform mass that gives a downward pull to a patient in which said mass can be accurately determined, so that the user/patient is not given too large or too small an amount of weight.

It is a further object of this invention to provide an appliance having a means to attach to a person's forearm, with a plurality of loops, where the plurality of loops are formed from a single continuous piece of resilient strap.

BRIEF DESCRIPTION OF THE DRAWINGS

FIG. 1 is a prospective view of the orthopedic appliance that is in a position ready to receive a user's forearm, with a dumbbell adjacent to said orthopedic appliance in a position so that it is able to be inserted into one of the loops.

FIG. 2 depicts the loop in FIG. 1 in which the dumbbell is inserted into said loop.

FIG. 3 depicts a user with the orthopedic appliance attached to their forearm, with a series of dumbbell weights inserted through a series of loops on the orthopedic appliance.

FIG. 4 depicts a cross-sectional view of the single strap that can be formed into a series of loops, where said drawing shows the folding that is done to the strap to provide loops of various incremental lengths.

FIG. 5 is a diagram of a continuous strap showing the points at which the strap would be folded on itself.

FIG. 6 depicts a diagram of the continuous strap showing the lengths of each of the loops when folding is done according to that shown in FIG. 5.

FIG. 7 depicts an alternate method of providing weights for this orthopedic appliance, using a weighted mass and an extender having a hook shaped end that attaches to U-shaped loops fixed on the forearm strap, with the second L-shaped end able to receive disk shaped weights defining a hold for the L-shaped end to pass through.

DESCRIPTION OF PREFERRED EMBODIMENT

Referring now to FIG. 1, an orthopedic appliance 10 is shown comprising a length of strap or belt (belt) 50 that has been formed into one or more descending loops 15, 16 and 17. The looped belt 50 has a top portion 80 that is attached to least one forearm strap 11. Said looped belt 50 and forearm strap 11 are attached together using such methods as stitching, detachable snaps, or Velcro type surfaces. Preferably, the forearm strap 11 and belt 50 are stitched together, using a resilient thread so as to prohibit any undesired movement between the belt 50 and forearm strap 11.

The forearm strap 11 should be made of a resilient material that yields to bending or folding, so that it can encircle a patient's forearm and apply a slight amount of circumferential pressure to the forearm. The forearm strap 11 has an inner side 12 and outer side 13, and an overall length sufficient to encircle a person or patient's forearm 30. The forearm strap has a means to attach the outer side 13 to the inner side 12 of the forearm strap 11, so as to be able to wrap snugly around a user's forearm 30 as shown in FIG. 3. Preferably, the forearm strap 11 should be adjusted so that it fits snugly against a patient's forearm, and is limited in the size of loop it defines, so that the patient's descending portion of the arm that is hanging down below where the appliance 10 is wrapped around the arm cannot readily slip through. For example, the forearm strap 11 could be wrapped around the upper portion of a patient's arm, with the elbow joint serving the same function as the hand as is described for this invention. This would be necessitated in a situation where a patient had suffered injury to their wrist or hand, and were unable to have pressure applied at those points. The forearm strap 11 will therefore be all that is required to keep this appliance in position on the patient's body.

The means to attach the outer side 13 to the inner side 12 of the forearm strap 11, as shown in FIGS. 1 and 3, depicts the inner side 12 has a Velcro type receiving surface or loops, with the outer side 13 of the forearm strap 11 having the Velcro type hooks that are able to engage and attach to the Velcro receiving surface loops located on the inner side 12 of the forearm strap 11.

It is not intended that the means to attach the forearm strap 11 to itself is limited in the scope of this patent to using Velcro type surfaces. Any other means commonly known in the art may be used, such as snaps, buckles or other means common to fixing straps and their ends one to another may be used.

Preferably, there are a pair of forearm straps 11 situated so that they are positioned parallel to each other, so that if one forearm strap 11 becomes unintentionally unfastened, the second forearm strap 11 will maintain a grip on the user or person's forearm 30 in the same fashion as the first forearm strap.

The forearm strap 11 is attached to a belt 50, where the belt 50 is folded so as to define at least one loop 17. The belt 50 should be made out of a resilient material that is not prone to elongate under stress. The belt 50 is typically and preferably comprised of a thick nylon material that resists stretching and degradation due to liquids or other foreign substances. The belt 50 should also have a weight carrying capacity of at least twenty-five pounds.

The belt 50 is folded over onto itself to create a loop 17, which defines and encircles a space within the loop 17. The loop 17 must define a space that is capable of receiving a weighted material, preferably able to receive the bulbous end 22 of a dumbbell 20. The dumbbell 20 is comprised of two weighted bulbous ends 22, that are spaced apart from each other by a rigid hand grip 21, where the hand grip 21 has a circumference less than that of either bulbous end 22. When using a dumbbell 20 for the weighted material, the width of the belt 50 should be approximately that of a hand grip 21 of a dumbbell 20 with the width of the belt 50 not exceeding the length of the hand grip 21 of the dumbbell 20.

Preferably, loops 17, 16 and 15 are each defined by a length of belt 50, with the belt 50 for each loop 17, 16 or 15 folded back 180 degrees upon itself to create a unshaped length having an open end. Attaching the open ends to each other to form a closed loop end 80, creates a continuous loop in the strap, 15 as shown by 17, 16 and 15. The loop 15 and loop 16 should define and encircle an area that can accommodate a dumbbell 20 in a manner similar to and as described for the loop 17. The width of the belt 50 used to form loop 16 and loop 15 should be no greater than the length of the hand grip 21 of the dumbbell 20 that it is intended to receive.

The ends of each additional unshaped loop 16 and 15 are attached together to define a closed loop end 80, with the closed loop ends 80 of any loop 17, 16 and 15 attached to each other, so that any folds defining the closed loop ends 80 are adjacent to one another. The loop closed ends 80 may be closed by means of stitching, adhesive bonding, stapling or any other means commonly known or used in the art of attaching one length of a belt 50 to another length of a belt 50.

At the point where the loop closed ends 80 are attached together, one or more forearm straps 11 are affixed thereto, using any common attachment means to permanently affix the forearm straps 11 to the loop closed ends 80. The forearm straps are preferably oriented perpendicularly to the length of the belt 50 defining any of the loop 17 and additional loops 16 and 15 used in this orthopedic appliance 10.

Referring also to FIG. 2, the belt 50 is shown defining the area of a loop 17 that can receive a dumbbell 20. This depiction would be identical for any additional loops, such as 16 and 15 being utilized with this orthopedic appliance 10. Preferably, a dumbbell 20 or other similar unit of weight having a known mass is to be used with this orthopedic appliance 10. A dumbbell 20 is a preferred type of mass unit to be used, since in addition to it having a stated or known mass, it has a shape that is particularly adapted to receiving a belt 50 forming to a loop 17, 16 or 15 around its hand grip 21. As shown in FIG. 2, once the dumbbell 20 is placed into the space defined by a loop 17, 16 or 15, and supported by said loop 17, 16 or 15, the bulbous ends 22 of the dumbbell 20 should protrude outward from either side of the belt 50 defining the loop 17, 16 or 15. The larger circumference of the bulbous end 22, as related to the hand grip 21, will prevent sideway slippage of the dumbbell 20 through the loop, so that the dumbbell 20 will remain securely held within the loop. Referring also to FIG. 3, a person is shown laying on a table 31 with their forearm 30 extended directly downward in the direction of the direction of pull 32. The orthopedic appliance 10 is attached to the forearm 30 with at least one dumbbell 20 situated within a loop 17. The particular orthopedic appliance 10 shown has three loops 17, 16 and 15, which can receive a dumbbell 20 in each loop 16 and 15.

The force of gravity causes the dumbbell 20 to be urged in the direction of pull 32, so that the force applied to the forearm 30 is always in a directly downward direction of pull 32. The orthopedic appliance 10 is affixed to the forearm 30, using the forearm straps 11 that are wrapped around and affixed to each other utilizing the attachment means on the ends of the forearm strap 11.

The person utilizing this forearm strap 11 should lay in the position indicated in FIG. 3, with the direction of pull 32 being applied to the forearm 30 so that the direction of pull 32 is acting on the shoulder area of the person. The person laying in this position, should remain so situated for anywhere from ten to fifteen minutes, muscle relaxation being a priority. There is no effort required to hold onto or maintain the attachment of the orthopedic appliance 10 to the person's forearm 30, since the forearm strap 11 securely is fastened about forearm 30. The dumbbell 20 or weighted material used should create a general pulling weight of anywhere from ten to a maximum of twenty-five pounds, which would provide a force in the direction of pull 32 on the person's forearm 30. The amount of mass used will be dependent on the type of injury reported by the person, the size of the person, and the duration of the time that the orthopedic appliance 10 is applying a force in the direction of pull 32 for the patient.

This orthopedic appliance 10 maximizes the benefits it offers by creating a direction of pull 32 through the center of the forearm 30, so that the direction of pull 32 is directly downward from the main mass of the forearm 30 and the person's upper body and shoulder. No means is provided to allow or require a patient to grip anything with their hand, so that a minimum of muscular stress is required to use this apparatus 10. As is also shown in FIG. 3, fingers and hands of a person using this invention are able to remain in a relaxed position, in that their hand does not need to grip or hold any part of said appliance. The length of the loop 17, from the loop closed ends 80, to the position of the weighted material, or weighted unit of mass such as a dumbbell 20, allow the weighted material to swing into position so that the force of gravity positions it directly below the person's forearm 30, at the point where the orthopedic appliance 10 is attached to the forearm 30. This provides a direction of pull 32 that is transferred to the shoulder area, with the direction of pull 32 being oriented through the center of the forearm 30 at the point where the orthopedic appliance 10 is wrapped around the forearm 30.

Referring to FIG. 4, which is a cross sectional view of a belt 50, the single belt 50 can be folded and oriented to itself so that a plurality of loops 17, 16 and 15 are formed. Referring also to FIGS. 5 and 6, the approximate location of folds made along the length of the belt 50 are shown.

FIG. 5 depicts a single belt 50 having various folds designated along its length. A segment is defined by a portion of the length of belt 50 from one end to a fold line, or from one fold line to another fold line. A first segment 41 is created on the belt 50, by causing the belt 50 to be folded 180 degrees at approximately the point designated as the first fold 51 along the length of belt 50. The first segment 41 comprises approximately one half of loop 15, with the first segment 41 defined by the distance from the belt's first end 70 to the first fold 51. The unit length of loop 15, the unit length of loop 16 and the unit length of loop 17 are all defined in relationship to each other by a unit of measurement "X", where the first segment 41 and second segment will each have an approximate length of 3X. The third segment 43 and fourth segment 44 will each have an approximate unit length of 4X, and the fifth segment 45 and sixth segment 46 will each have an approximate unit length of 5X.

Following the fold 51, which orients the first segment 41 approximately 180 degrees to the remaining portion of the belt 50, so that the second segment 42 is oriented immediately adjacent to first segment 41. The second segment 42 is defined as the distance from the first fold 51 to the second fold 52, with the second segment 42 having a slightly greater length than the first segment 41.

A second fold 52 is made so that the belt 50 is folded back 180 degrees with the third segment 43 being placed adjacent to the first segment 41, with the first segment 41 situated between the second segment 42 and the third segment 43. The second segment 42 is defined as the length of belt 50 from the first fold 51 to the second fold 52.

A third fold 53 is then made with the fourth segment 44 being placed adjacent to the third segment 43 so that the third segment 43 is now situated between the first segment 41 and fourth segment 44. The third segment 43 and fourth segment 44 should have a length that is approximately equal to each other, but which is a greater length than the first segment 41 or second segment 42. The third segment 43 is defined as the length of belt 50 from the second fold 52 to the third fold 53.

A fourth fold 54 is then made orienting the belt 50 so that the fifth segment 45 is placed adjacent to the fourth segment 44. The fourth segment 44 is defined as the length of belt 50 from the third fold 53 to the fourth fold 54.

A fifth fold 55 is then made with sixth segment 46 being positioned so that it is placed in between the fifth segment 45 and the fourth segment 44. The fifth segment 55 is defined as the length of belt 50 from the fourth fold 54 to the fifth fold 55, and the sixth segment defined as the length of belt 50 from the fifth fold 55 to the belt second end 70a.

The overlapping portions of the length of the belt 50, being the top end or end portion of the loops 15, 16 and 17, are attached together at approximately point 81, which bisects one of the end of each of the various segments 41, 42, 43, 44, 45, and 46. In this manner, a loop 17, loop 16, and loop 15 are formed, each defining a space to receive a weighted object, such as a dumbbell 20 with the loop closed ends 80 defining a uniform area of attachment of the segments to each other.

The use and description of loop 17, loop 16 and loop 15 are for illustrative purposes only. This is not intended to limit the scope of this invention to three loops, but is intended to show that a plurality of loops can be made and used in which one or more dumbbells 20 may be inserted in a plurality of loops. This orthopedic appliance 10 will operate in the same fashion with a single loop such as loop 17. Additional loops 16 and 15 are useful in that they allow dumbbells 20 of various masses to be inserted therein to each of them, thereby allowing an adjustment of mass to provide varying forces in the direction of pull 32.

Referring to FIG. 6, a front view of the belt 50 is shown in which the second segment 42 covers a portion of the third segment 43, with the third segment 43 covering a portion of the sixth segment 46. The loops 15, 16 and 17 and their relationship to each other is exemplified by this figure. The approximate length of the second segment 42, third segment 43 and sixth segment 46 are also shown as designated by unit length of the first loop 15, the unit length of the second loop 16 and the unit length of the third loop 17. The unit measurements of the unit length of the first loop 15, the unit length of the second loop 16 and the unit length of the third loop 17 are not intended to limit the scope of this invention as to any particular length, but are only used for illustrative purposes to show that a third loop 17 and one or more second loops and/or loop are to have varied lengths so as to accommodate one or more dumbbell 20 as shown in FIG. 3.

Referring to FIG. 7, an alternate means to attach weight to the forearm straps 13 is shown. The appliance 10 has one or more loop holders 75 attached, which support U-shaped loops. The loop holders 75 may be constructed from material similar to the belt 50, and may be attached to the belt by any ordinary means. Typically, and preferably, the loop holder 75 will be stitched to the forearm strap 13, with the unshaped loops 74 able to pivot upward and downward.

An extender 77 is used to support the added weight units, which in FIG. 7 is depicted as a disk weight 78, having a centrally located hole 79. This type of weight 78 would be most commonly used with weight training equipment, and used on a weight bar in conjunction with other weights of various mass units.

The extender 77 has a central elongated shaft 71, with a top curved hook shaped end 73, and a bottom L-shaped end 72. The central elongated shaft 71 may be constructed out of metal or any other type of resilient material capable of supporting a pulling force of at least fifteen pounds, up to the maximum weight to be used with this appliance 10. While the elongated shaft 71 may be flexible, thee top end 73 and bottom end 72 must remain rigid to properly support the pulling force of the weight or mass units placed upon it.

The curved hook end 73 must have a diameter that allows the end 73 to be placed through a unshaped loop 74, so that the extender 77, and any weight 78 placed upon it will hang from and be supported by the unshaped hook 74. A plurality of extenders 77 may be used with the appliance 10, if a plurality of loop holders 75 and unshaped loops 74 are available on the forearm strap 13. The extender may provide an L-shaped end 72 to receive weight 78, but the extender 77 itself may also be constructed so that the weight of the extender 77 itself provides the necessary weight for the appliance 10.

From the foregoing statements, summary and description in accordance with the present invention, it is understood that the same are not limited thereto, but are susceptible to various changes and modifications as known to those skilled in the art and we therefore do not wish to be limited to the details shown and described herein, but intend to cover all such changes and modifications which would be encompassed by the scope of the appended claims.

I claim:

1. An orthopedic appliance that is designed to assist in the reduction of an anterior dislocation of a patient's affected appendage while the appendage is hanging downward during the reduction treatment, where the patient does not use their hand to grip or hold any part of said appliance, comprising:

a. One or more forearm straps that are able to fully encircle the patient's forearm, having a means to secure the ends of said forearm straps to provide a closed loop of desired size that can accommodate the person's forearm; and b. A means to support a weighted unit, fixed to said forearm strap, where the weighted unit is able to be supported so that it is positioned below the wrist of a patient using this appliance, where said means to support a weighted unit comprises multiple loops, where each of the loops have different lengths with a common point of attachment to the forearm strap, so that each of the three loops can independently support a weighted mass.

* * * * *